(12) United States Patent
Miyamoto et al.

(10) Patent No.: US 9,085,758 B2
(45) Date of Patent: Jul. 21, 2015

(54) METHOD OF CULTURING VASCULAR SMOOTH MUSCLE CELLS, CULTURE DEVICE AND MEDICAL MATERIAL OBTAINED BY THE CULTURE

(75) Inventors: Keiichi Miyamoto, Mie (JP); Takashi Horiuchi, Mie (JP)

(73) Assignee: JNC CORPORATION, Tokyo (JP)

( * ) Notice: Subject to any disclaimer, the term of this patent is extended or adjusted under 35 U.S.C. 154(b) by 129 days.

(21) Appl. No.: 13/613,206

(22) Filed: Sep. 13, 2012

(65) Prior Publication Data

US 2013/0029420 A1    Jan. 31, 2013

Related U.S. Application Data

(62) Division of application No. 12/227,688, filed as application No. PCT/JP2007/060604 on May 24, 2007.

(30) Foreign Application Priority Data

May 25, 2006  (JP) ................. 2006-144909

(51) Int. Cl.
| | |
|---|---|
| C12N 5/00 | (2006.01) |
| A01N 1/00 | (2006.01) |
| C12N 5/071 | (2010.01) |
| A61L 27/22 | (2006.01) |
| A61L 27/38 | (2006.01) |
| A61L 27/50 | (2006.01) |
| C12M 1/12 | (2006.01) |
| A61K 35/12 | (2015.01) |

(52) U.S. Cl.
CPC ............. *C12N 5/0691* (2013.01); *A61L 27/227* (2013.01); *A61L 27/383* (2013.01); *A61L 27/3826* (2013.01); *A61L 27/3895* (2013.01); *A61L 27/507* (2013.01); *C12M 25/02* (2013.01); *A61K 35/12* (2013.01); *C12N 2533/50* (2013.01)

(58) Field of Classification Search
CPC .................................................. C12N 5/0068
USPC .................................................. 435/1.1, 395
See application file for complete search history.

(56) References Cited

U.S. PATENT DOCUMENTS

2004/0136977 A1    7/2004  Miyamoto

FOREIGN PATENT DOCUMENTS

| JP | 2002-531118 | 9/2002 |
| JP | 2002-335955 | 11/2002 |
| JP | 2003-189843 | 7/2003 |
| WO | 02/35992 | 5/2002 |
| WO | 02/096978 | 12/2002 |

OTHER PUBLICATIONS

Yamamoto et al. (1994, Connective Tissue, vol. 26, pp. 245-254).*
Wilson et al. (1995, JCI, vol. 96, pp. 2364-2372).*
Black et al. (2005, J. Appl. Physiol., vol. 98, pp. 1434-1441).*
International Search Report issued Jul. 10, 2007 in the International (PCT) Application PCT/JP2007/060604.
Keiji Naruse et al., "Involvement of SA channels in orienting response of cultured endothelial cells to cyclic stretch", Am. J. Physiol., 274:H1532-1538, 1998.
Keiichi Miyamoto et al., "Immobilized gellan sulfate surface for cell adhesion and multiplication: development of cell-hybrid biomaterials using self-produced fibronectin", International Journal of Biological Macromolecules, vol. 30, pp. 75-80, 2002.
Kiyotaka Yamamoto et al., "Role of Elastin in the Differentiated Properties of Vascular Smooth Muscle Cells in Culture", Connective Tissue, vol. 26, No. 3, pp. 245-254, 1994.
Paula Engbers-Buijtenhuijs et al., "Biological characterisation of vascular grafts cultured in a bioreactor", Biomaterials, vol. 27, No. 11, pp. 2390-2397, Apr. 2006.
Eiichi Kitazono et al., "Tissue Engineering using Nanofiber", Journal of Synthetic Organic Chemistry, Japan, vol. 62, No. 5, pp. 514-519, 2004.
M. Cho et al., "Phenotypic changes of vascular smooth muscle cells in three dimensional collagen gel for the development of vascular graft was composed of biomaterials", The Japanese Journal of Artificial Organs, vol. 26, No. 5, pp. 946-951, 1997.
International Preliminary Report on Patentability including translation of PCT Written Opinion dated Dec. 24, 2008 in International (PCT) Application PCT/JP2007/060604.
Supplementary European Search Report issued Mar. 30, 2010 in corresponding European Patent Application No. 07 74 4038.
L. Buttafoco et al., "First Steps Towards Tissue Engineering of Small-Diameter Blood Vessels: Preparation of Flat Scaffolds of Collagen and Elastin by Means of Freeze Drying", Journal of Biomedical Materials Research, Part B, Applied Biomaterials, 2006, vol. 77, No. 2, pp. 357-368.
Joseph Berglund et al., "Incorporation of Intact Elastin Scaffolds in Tissue-Engineered Collagen-Based Vascular Grafts", Tissue Engineering, 2004, vol. 10, No. 9/10, pp. 1526-1535.
Laura Niklason et al., "Functional Arteries Grown in Vitro", Science, 1999, vol. 284, No. 5413, pp. 489-493.

(Continued)

*Primary Examiner* — Anoop Singh
*Assistant Examiner* — David A Montanari
(74) *Attorney, Agent, or Firm* — Wenderoth, Lind & Ponack, L.L.P.

(57) ABSTRACT

There is provided a method for culturing vascular smooth muscle cells while maintaining their normal function, and a culture device and regenerative medical material for the same. The method takes advantage of vascular smooth muscle cell recognition of elastin as an extracellular matrix. The invention provides a method for culturing vascular smooth muscle cells on elastin, a culture device having elastin anchored on the cell-growing surface, a culture device wherein the cell-growing surface is composed of an elastin molded article, and medical materials obtained by culturing vascular smooth muscle cells using such culture devices.

1 Claim, 6 Drawing Sheets

(56) References Cited

OTHER PUBLICATIONS

Laura Niklason et al., "Morphologic and mechanical characteristics of engineered bovine arteries", Journal of Vascular Surgery, 2001, vol. 33, No. 3, pp. 628-638.

Chrysanthi Williams et al, "Perfusion Bioreactor for Small Diameter Tissue-Engineered Arteries", Tissue Engineering, 2004, vol. 10, NR. 5/6, pp. 930-941.

Alpesh Patel et al., "Elastin biosynthesis: The missing link in tissue-engineered blood vessels", Cardiovascular Research, 2006, vol. 71, No. 1, pp. 40-49.

Jennie Leach et al., "Crosslinked alpha-elastin biomaterials: towards a processable elastin mimetic scaffold", Acta Biomaterialia, 2005, vol. 1, No. 2, pp. 155-164.

Yamamoto et al., Connective Tissue, 1994, vol. 26(3), pp. 245-254.

Kitazono et al., J. Synthetic Organic Chemistry, 2004, vol. 62(5), pp. 514-519.

Wilson et al., JC1, 1995, vol. 96, pp. 2364-2372.

Teng et al., J. Phys. Chem. B 2011, 115, pp. 1608-1615.

* cited by examiner

Fig. 1

Water-soluble elastin smooth muscle cell cytotoxicity test (n=9)

Fig. 2

DSP-activated dodecanedicarboxylic acid crosslinking agent smooth muscle cell cytotoxicity test (n=6-7)

Contact angles with corona discharge alone, corona discharge followed by elastin treatment, and corona discharge followed by collagen treatment. (**$P<0.0001$ vs. control)

Fig. 6

Contact angles with corona discharge alone, corona discharge followed by elastin treatment, and corona discharge followed by collagen treatment.

Fig. 7 a) adhesion and b) distension for vascular smooth muscle cells c) adhesion and d) distension for fibroblasts e) adhesion and f) distension for vascular endothelial cells ○: Collagen-coated dish
■: Elastin-coated dish
×: Corona discharge-treated dish

METHOD OF CULTURING VASCULAR SMOOTH MUSCLE CELLS, CULTURE DEVICE AND MEDICAL MATERIAL OBTAINED BY THE CULTURE

This application is a divisional of Ser. No. 12/227,688, filed Nov. 25, 2008, which is a 371 U.S. national stage of International Application No. PCT/JP2007/060604 filed May 24, 2007, herein incorporated by reference in their entirety.

TECHNICAL FIELD

The present invention relates to a method of culturing vascular smooth muscle cells, to a culture device therefor and to a medical material obtained by the culture.

BACKGROUND ART

Vascular graft replacement has come to be performed in recent years as surgical treatment for trauma and vascular diseases such as atherosclerosis, but artificial blood vessels have not been realized for small blood vessels with diameters of 5 mm and less. The reason is that obstruction due to thickening of the tunica intima of vascular grafts or thrombus formation cannot be prevented, because of the poor biocompatibility of artificial materials. The major bypass or vascular replacement technique currently used for elastic arteries such as coronary artery and lower leg peripheral arteries is autologous vein grafting. However, approximately 20-30% of all patients requiring vascular replacement do not have suitable blood vessels and are not candidates for autologous vein grafting.

In recent years, it has been attempted to coat extracellular matrixes such as collagen onto the lumen surfaces of artificial vessels made of synthetic fibers worked into small diameters (Dacron/polyurethane/drawn polytetrafluoroethylene), or onto the lumen surfaces of tubular structures formed from bioabsorbable synthetic polymers (for example, polyglycolic acid, polylactic acid, poly ϵ-caprolactam and the like), in order to provide them with a cell adhesion property, and to culture endothelial cells on those extracellular matrixes. However, small-diameter artificial vessels have not been realized because the endothelial cells do not become stably anchored to the extracellular matrix, or the artificial vessels undergo intimal thickening.

The blood vessel wall damage that occurs due to endothelial thickening causes smooth muscle cells near the endothelium to undergo a phenotypic change from the normal contractile to synthetic type, thus promoting growth and organization and extending the lesion. Numerous methods of culturing vascular smooth muscle cells have been investigated, as basic research on vascular smooth muscle. Examples thereof include a method of culturing solution containing insulin-like growth factor-I on a laminin-coated culture dish (for example, Patent document 1), and a method of fixing smooth muscle cells onto fibronectin-coated glass and applying shear flow stress for culturing, as a method that takes into account the orientation of the smooth muscle cells (for example, Patent document 2).

The present inventors have also developed a crosslinked elastin article having water-soluble elastin crosslinked with a water-soluble crosslinking agent, which can be applied as a biomaterial for regenerative medicine (Patent document 3). In this method, the crosslinked elastin article is utilized as a culture substrate for regenerative medicine, and embryonic stem (ES) cells, somatic stem cells, mesenchymal stem cells or the like are cultured on a film surface or tube interior made therefrom, to form organs having desired shapes. Culturing of neuroblastoma cells has been carried out using elastin films produced from crosslinked elastin articles, but no biomaterial has been disclosed with special affinity between elastin and vascular smooth muscle cells.

Since most cells in the body are present at sites that are subject to mechanical forces, dynamic culturing methods are also known whereby the cell-growing surface is expanded and contracted in order to accomplish cell culturing with growth under conditions similar to in vivo conditions (Non-patent document 1).

[Patent document 1] Japanese Unexamined Patent Publication No. 2002-335955
[Patent document 2] Japanese Patent Public Inspection No. 2002-531118
[Patent document 3] WO 02/096978
[Non-patent document 1] K. Naruse, T. Yamada, M. Sokabe, Am. J. Physiol. 274: H1532-1538 (1998) Involvement of SA channels in orienting response of cultured endothelial cells to cyclic stretch

DISCLOSURE OF THE INVENTION

Problems to be Solved by the Invention

A very strong demand exists for culturing methods and culture devices for vascular smooth muscle cells, to be used in basic research toward elucidation of the mechanism of endothelial thickening associated with vascular smooth muscle cells and observation of the reaction of vascular smooth muscle cells to drugs, and in the development of vascular grafts. It is an object of the present invention to provide a culturing method which facilitates growth of vascular smooth muscle cells, for example, and particularly a method and device for culturing of vascular smooth muscle cells while maintaining the normal types (differentiated types) of the vascular smooth muscle cells.

Means for Solving the Problems

The present invention is an application of the knowledge that vascular smooth muscle cells grow on elastin as a scaffold. The invention therefore relates to a method of culturing vascular smooth muscle cells characterized by culturing vascular smooth muscle cells on elastin. Vascular smooth muscle cells are subjected to mechanical stress in the body. In order to obtain cells with properties similar to in vivo vascular smooth muscle cells, therefore, it is preferred for the culturing to be carried out under dynamic conditions similar to in vivo conditions. Growth of vascular smooth muscle cells, however, requires initial growth under static conditions until the cells have become bound to the growing surface. According to a preferred mode of the culturing method, therefore, the vascular smooth muscle cells are cultured under static conditions in which the elastin neither expands nor contracts, until the vascular smooth muscle cells have become bound to the elastin, and then the vascular smooth muscle cells are cultured under dynamic conditions in which the elastin expands and contracts.

The invention also incorporates the knowledge that vascular smooth muscle cells grow more specifically on elastin, compared to other vascular cells. The invention therefore further relates to a method of culturing vascular smooth muscle cells by selective growth of the vascular smooth muscle cells, characterized by culturing a mixture of vascular smooth muscle cells and other vascular cells on elastin.

The invention still further relates to a culture device for vascular smooth muscle cells, having elastin anchored on a cell-growing surface. One mode thereof is a culture device for vascular smooth muscle cells wherein the elastin is anchored on a non-elastic material surface. Another mode thereof is a culture device for vascular smooth muscle cells wherein the elastin is anchored on an elastic material surface. Preferred is a culture device for vascular smooth muscle cells wherein the elastin is anchored onto a silicon rubber sheet. Since such culture devices are usually placed under microscope observation, the transmittance of the cell-growing surface for visible light or ultraviolet light is preferably 50-100%.

The invention still further relates to a culture device for vascular smooth muscle cells, wherein the cell-growing surface is composed of a molded crosslinked elastin article. The transmittance of the cell-growing surface of the culture device for visible light or ultraviolet light is preferably 50-100%.

The invention yet further relates to a medical material obtained by culturing vascular smooth muscle cells using a culture device for vascular smooth muscle cells that has elastin anchored on a cell-growing surface, and to a medical material obtained by culturing vascular smooth muscle cells on a molded crosslinked elastin article obtained by crosslinking water-soluble elastin.

Effect of the Invention

By culturing vascular smooth muscle cells on elastin, and especially by using a culture device having elastin anchored on the cell growth surface for the culturing, it is possible to accomplish selective culturing of vascular smooth muscle cells, and to accomplish the cell culturing while maintaining the normal type (differentiated type) of the vascular smooth muscle cells. In addition, it is possible to produce a medical material by culturing the vascular smooth muscle cells on the elastin-anchored culture device or molded crosslinked elastin article.

BEST MODE FOR CARRYING OUT THE INVENTION

Arterial vascular walls have a three-layer structure comprising an intima, media and adventitia, and it is a muscular tissue structure with smooth muscle cells as the major components. The intima which directly contacts with the blood has a monolayer squamous epithelium of endothelial cells and, directly under it, a subendothelial layer consisting of a basement membrane, loose connective tissue and a small number of longitudinal smooth muscle cells. The endothelial cell layer covers the vascular lumen, and is oriented in such a manner the cell long axes are parallel to the direction of blood flow. The media is the blood vessel wall and the thickest layer, and the concentric cell layers composing it are made of smooth muscle cells oriented parallel to the pulsating direction. The smooth muscle cells perform the important function of maintaining blood pressure and controlling the distribution of blood flow. Between the unstriated muscle layers there are found elastin fibers, type III collagen and proteoglycans, conferring arteries with the additional property of contracting during cardiac systole due to the abundant elastin in the arterial walls. Between the intima and media lies a structure composed of a fenestrated homogeneous elastin layer, known as the internal elastic lamina. The adventitia is composed mainly of fibroblasts, collagen fibers and longitudinal elastic fibers, and a fenestrated homogeneous elastin layer known as the external elastic lamina is likewise present between the media and adventitia.

Thus, the vascular smooth muscle is in an intimate relationship with elastin layers, and therefore when vascular smooth muscle cells are cultured with a culture device comprising an elastin layer, the elastin acts as a scaffold for the vascular smooth muscle cells. In addition, since elastin forms tissue that surrounds vascular smooth muscle cells in the body, it is conjectured that the binding of the vascular smooth muscle cells to elastin in the vascular wall media structure and their presence in the elastin matrix while being subjected to mechanical stimulation in the body, are the factors responsible for the normal type of smooth muscle cells. Consequently, culturing of vascular smooth muscle cells on elastin can be accomplished under conditions similar to in vivo tissue, thus suitably maintaining the normal type (differentiated type).

The first aspect of the invention relates to a method of culturing vascular smooth muscle cells, characterized by culturing vascular smooth muscle cells on elastin.

One mode thereof comprises culturing vascular smooth muscle cells with a culture device having elastin anchored on a cell-growing surface. Another mode employs a molded crosslinked elastin article as the cell-growing surface.

Any elastin may be used for the invention, including water-soluble elastin, water-insoluble elastin and crosslinked elastin obtained by crosslinking water-soluble elastin with a crosslinking agent. According to the invention, water-soluble elastin and crosslinked elastin according to the invention are preferable for ease of use.

Cell culturing methods include dynamic culturing and static culturing. Dynamic culturing involves culturing while contracting and expanding the surface on which the cells grow. Dynamic culturing according to the invention is therefore a method of culturing wherein elastin is anchored onto the cell-growing surface, i.e. the surface on which the culture solution is placed, and the surface is repeatedly contracted and expanded. Most cells in the body are located in areas subject to dynamic forces, and function while being exposed to dynamic environmental changes. In the case of blood vessels, shear flow stress is produced in the endothelial cells composing the vascular wall, and periodic tensile load is exerted on the vascular smooth muscle cells and fibroblasts that do not contact with the blood flow. Culturing under conditions similar to vascular smooth muscle cells in the body is dynamic culturing. Dynamic culturing with vascular smooth muscle cells placed under mechanical stress is effective for observing whether dedifferentiation occurs, or for observing the phenomenon of cellular orientation.

Static culturing is a common culturing method with the cell-growing surface in a static state, i.e. without expansion or contraction. This culturing method is carried out under conditions that are different from the in vivo environment, but it is still useful as a method for examining the basic properties of vascular smooth muscle cells. However, ordinary static culturing is known to cause vascular smooth muscle cells to dedifferentiate to the synthetic form, and to promote proliferation. Since cells in this state are not the normal in vivo type, it must be kept in mind that false conclusions can be drawn when they are utilized for drug screening or as a cell culture model for tissue regeneration.

During culturing of vascular smooth muscle cells, the cells proliferation after attaching to the bottom of the culture device. Even with dynamic culturing, static culturing must be carried out until the vascular smooth muscle cells attach to the bottom of the culture device. Therefore, the most advantageous culturing method for vascular smooth muscle cells according to the invention is a method in which the vascular smooth muscle cells are statically cultured until they bind to elastin, and then dynamically cultured by expanding and contracting the cell-growing surface to which the elastin is anchored.

The culturing temperature and carbon dioxide gas concentration for static culturing and dynamic culturing may be according to ordinary conditions, preferably with a temperature of approximately 37° C. and a carbon dioxide gas concentration of approximately 5%. A standard frequency for expansion and contraction for dynamic culturing is 0.5 Hz, i.e. one cycle every 2 seconds, but this frequency may be higher or lower. The expansion and contraction may be unaxial stretch in a single direction or biaxial stretch in two directions. The degree of expansion and contraction is generally about 5-50% of the length of the cell-growing surface, but this may be varied depending on the needs of the study. The degree of expansion and contraction is determined in relation to its frequency.

The second aspect of the invention is to provide a method of selectively culturing vascular smooth muscle cells, characterized by culturing a mixture of vascular smooth muscle cells and other vascular cells (vascular endothelial cells, vascular smooth muscle cells, fibroblasts, hemocytes, macrophages or the like) on elastin. Using elastin as the surface substance allows specific growth of vascular smooth muscle cells, as opposed to most of the major extracellular matrix substances such as collagen, fibronectin and laminin. It is believed that only the smooth muscle cells recognize elastin among the vascular cells. On the other hand, all cell types bind and distend on collagen without specificity. Utilizing this property, a mixture of vascular smooth muscle cells with other vascular cells on elastin can accomplish growth of the vascular smooth muscle cells alone. Presumably, elastin-recognizing receptors on the vascular smooth muscle cell surfaces play an important role in this growth.

The third aspect of the invention is to provide a culture device for vascular smooth muscle cells by the culturing method described above. As a feature of the culture device of the invention, elastin is used on the surface on which the vascular smooth muscle cells are to be grown (the surface on which the culture solution is placed). The elastin anchored to the cell-growing surface acts through cell surface receptors to participate in extracellular matrix recognition in signal transduction of vascular smooth muscle cell activity, thus providing a very favorable environment for growth of the vascular smooth muscle cells.

The material of the cell-growing surface on the culture device may be elastin anchored on a plastic or silicon rubber sheet, or an elastin molded article produced by crosslinking of water-soluble elastin.

For static culturing alone, a non-elastic plastic material such as polystyrene, polycarbonate, polypropylene or polyacrylonitrile may be employed. For dynamic culturing, any material that can withstand repeated expansion and contraction may be employed, such as silicon rubber, natural rubber, acrylic rubber, polyurethane rubber or the like. An elastin molded article produced by crosslinking water-soluble elastin is elastic and can therefore be used for dynamic culturing. Materials that can be used for dynamic culturing can, of course, also be used for static culturing.

For basic research on vascular smooth muscle cells carried out under microscope observation, it is preferred for the material of the cell-growing surface to be transparent. The transmittance of the cell-growing surface for visible light or ultraviolet light is most preferably 50-100%. In some cases, however, the material will not need to be transparent, and the material may therefore be selected without regard to transparency.

The water-soluble elastin used for the invention can be obtained by hydrolysis of elastin, and specifically, it may be one or more types of elastin such as α-elastin or β-elastin obtained by hot oxalic acid treatment of animal cervical ligaments, κ-elastin obtained by alkali ethanol treatment of elastin, water-soluble elastin obtained by enzyme treatment with elastase, or tropoelastin as a precursor of the elastin biosynthetic pathway. Water-insoluble elastin is commercially available, and it may be subjected to hot oxalic acid treatment to obtain water-soluble elastin.

For anchoring of the elastin onto the culture device, the cell-growing surface, i.e. the surface on which the culture solution is to be placed, may be chemically or physically activated, a water-soluble elastin solution placed thereover and the activated surface allowed to react with the water-soluble elastin for a fixed period of time, and then the excess elastin solution discarded and the surface dried.

The anchoring reaction may be based on a commonly known chemical reaction (hydrogen bonding, ionic bonding, covalent bonding), or a radical bonding reaction.

The method of activating the surface of the culture device may be any method that generates highly reactive functional groups (amino, aldehyde, epoxy, carboxyl, hydroxyl, thiol groups, etc.) or radicals. For example, the inactive surface may be treated by carbonylation or carboxyl group introduction with a chemical agent such as chromic acid, sulfuric acid or hypochlorous acid, or by coating with a silane coupling agent containing functional groups, for activation of the culture substrate surface. As examples of silane coupling agents there may be mentioned γ-aminopropyltriethoxysilane, N-β-(aminoethyl)-γ-aminopropyltrimethoxysilane and N-β-(aminoethyl)-γ-aminopropylmethyldimethoxysilane. There may also be employed a method of polymer coating, such as the method of covering the inactive surface with, for example, polyacrylic acid containing added azide groups to introduce active groups, as described in Japanese Unexamined Patent Publication No. 2003-189843. This allows anchoring by photoreaction to be accomplished by pre-azidation of the elastin to be anchored. It is also effective to accomplish anchoring by the surface activation method via introduction of functional groups (mainly amine groups) using ammonia plasma as described by Miyamoto et al. in Int. Biol. Macromol., 30, 75-80 (2002). The water-soluble elastin is preferably reacted immediately after activation of the inactive surface by corona discharge treatment. For corona discharge treatment, the material with the inactive surface is placed on a glass base, and the tip of the corona flame blow-out point is brought to a position about 5-10 mm distant, and the corona flame is discharged onto the material surface (approximately 9 kV) for about 10-40 seconds. Within several hours, active radicals disappear from the surface that has been activated by corona discharge at the activation sites other than the locations where the water-soluble elastin has been anchored, thus restoring the inactive surface. This prevents anchoring of other substances present in the culture solution during growth of the cells, in order to facilitate a continuous effect of the elastin-anchored surface.

Since the water-soluble elastin is anchored by reaction with the surface-treated material as described above, it does not elute into the culture solution when subsequently contacted with the culture solution.

Another preferred mode of the culture device of the invention is a culture device for vascular smooth muscle cells employing a molded crosslinked elastin article having water-soluble elastin crosslinked on the cell-growing surface (bottom). A crosslinked elastin article having water-soluble elastin crosslinked with a crosslinking agent can be produced by the method described in WO 02/096978. The molded crosslinked elastin article produced by this process is contractile and porous (spongy). The crosslinked elastin article can then be shaped into a transparent sheet. The culture device having such a material as the cell-growing surface is suitable for static culturing and dynamic culturing of vascular smooth muscle cells. By forming it to an elastin concentration of at least 50% as the weight ratio, it is possible to inhibit the coacervation phenomenon that is a characteristic property of water-soluble elastin, and thus obtain a gel sheet with high optical transparency. Since the elastin molded article is porous, the three-dimensional culturing condition of the vascular smooth muscle cells can be observed under a microscope.

A preferred crosslinking agent for the water-soluble elastin is one represented by the following general formula.

[Chemical Formula 1]

<General Formula>

In the formula,
$R_1$ and $R_3$ are <A> or <B> represented by the following structural formula, and $R_1$ and $R_3$ may be either the same or different,

[Chemical Formula 2]

<A>

(wherein $R_4$ and $R_5$ are H, $CH_3$ or $C_2H_5$, and $R_4$ and $R_5$ may be either the same or different)

[Chemical Formula 3]

<B>

(wherein $R_2$ is a compound <C> or <D> represented by the following structural formula)

[Chemical Formula 4]

<C>

(wherein n is an integer of 1-20)

[Chemical Formula 5]

<D>

(wherein m and l are integers of 0-15, X and Y are $CH_2$ or O, X and Y being either the same or different, Z is C or N, and $R_6$, $R_7$, $R_8$ and $R_9$ are H, $CH_3$ or $C_2H_5$, and may be either the same or different).

The apparatus used for dynamic culturing is made of an elastic material capable of expanding and contracting the entire culture device containing the culture solution. It employs an elastic material having elastin attached to the cell-growing surface, or an elastic elastin molded article composed of crosslinked elastin. Any desired shape may be used. When expansion and contraction are applied uniaxially, a quadrilateral shape is most advantageous. A hexagonal shape may be employed to obtain non-uniformity for the directions of expansion and contraction. A quadrilateral culture device is produced by forming a rectangular box-like enclosure using a relatively thick material that can withstand repeated expansion and contraction, such as a thick natural rubber or silicon rubber sheet. According to one mode, a thin silicon rubber sheet is attached to the enclosure with an adhesive, and then the cell-growing surface is activated by corona discharge or the like to anchor the elastin. According to another mode, a crosslinked elastin sheet is attached to the bottom of the enclosure. For expansion and contraction of the entire culture device, a tensile tool is loaded at the opposing enclosure sections.

The apparatus for dynamic culturing may be cylindrical with stopped ends. A hole is formed at one of the stopped ends, a tool that applies expansive force and contractive force is fitted near the opening, and the culture solution is added through the opening for rotated culturing, to allow growth of the vascular smooth muscle cells only inside the cylindrical section. When cylindrical silicon rubber is used, only the inner surface is surface treated and elastin is anchored thereto. Alternatively, a cylinder may be formed with crosslinked elastin and the vascular smooth muscle cells grown on the inner surface.

A commercially available apparatus such as one by Strex, Inc., may be used as a dynamic culturing apparatus that expands and contracts the cell-growing surface. There may also be used a combination of apparatuses employing a linear actuator and linear slider.

The fourth aspect of the invention is a medical material obtained by culturing vascular smooth muscle cells on elastin. One mode thereof is obtained by culturing vascular smooth muscle cells using a culture device having elastin anchored on a cell-growing surface. For example, only the inner surface of a silicon rubber tube is activated by a chemical method and elastin is anchored thereto, and the tube is rotated in the culture solution while repeating expansion and contraction, so that only the inner surface becomes coated with vascular smooth muscle cells and can be used as a vascular graft.

Another mode is a medical material obtained by culturing vascular smooth muscle cells on a molded crosslinked elastin article obtained by crosslinking water-soluble elastin. A sheet is formed of elastin gel comprising crosslinked water-soluble elastin, and is attached to the bottom of a rectangular box-like enclosure formed of, for example, natural rubber or silicon rubber, to construct box-shaped culture device. After culturing the vascular smooth muscle cells, the section on which the vascular smooth muscle cells have grown may be cut out and directly applied as a material for in vivo implantation. As another example of using molded crosslinked elastin, a tube of approximately the size of a small-diameter artery may be formed of crosslinked elastin, and vascular smooth muscular tissue uniformly cultured and grown on the inner surface thereof, to produce a tissue engineering graft as a substitute small-diameter artery. A wide variety of uses are possible for biomedical materials obtained by culturing and growing vascular smooth muscle cells on elastin. A material obtained by a method of culturing vascular smooth muscle cells using crosslinked elastin according to the invention can be utilized for treatment of patients that are normally not candidates for vascular replacement techniques.

EXAMPLES

The present invention will now be explained in greater detail by examples, but the methods described hereunder were employed merely to confirm the effect and are not intended to be restrictive, while they may also be carried out with various modifications so long as the gist is maintained.

Production Example 1

Production of Water-Soluble Elastin

Defatted porcine aorta was washed with water and then immersed in 5-10 wt % aqueous sodium chloride and allowed to stand for 24 hours in a refrigerator, for dissolution and removal of the collagen. After washing, water was added and the mixture was boiled for 1 hour with a pressure cooker, after which the vascular accretions were removed and the mixture was placed in a mixer for crushing to a tissue fragment size of 1-5 mm. It was then heated for 1 hour in the pressure cooker and washed with water. After transfer to a meshed bag and washing with an electric washer, ethanol was added to a final concentration of 50 vol % and the mixture was allowed to stand for 30 minutes. Ethanol was then added to a final concentration of 70 vol % and the mixture was allowed to stand for 90 minutes. Ethanol was then further added to a final concentration of 90 vol % and the mixture was allowed to stand for 10 hours. Finally, the ethanol was removed and the product was dried under reduced pressure in a desiccator to obtain insoluble elastin (yield: approximately 330 g by dry weight from 2 kg of blood vessels). After adding 45 mL of 0.25 M oxalic acid to 10 g of the insoluble elastin, the mixture was heated at 100° C. for 1 hour. This was cooled with ice water and subjected to centrifugal separation, and the supernatant was collected and dialyzed against deionized water in a dialysis tube with a molecular weight of 10,000-14,000 to an external solution pH of about 5-6 for removal of the oxalic acid.

The supernatant was subjected to suction filtration with a glass filter, and the filtrate was lyophilized to obtain water-soluble elastin (approximately 3 g).

Production Example 2

Production of Crosslinking Agent

A chemical crosslinking agent was prepared by the method described in WO 02/096978, for production of an elastin structure using water-soluble elastin. The method involves active esterification of the carboxyl groups of dodecanedicarboxylic acid with 4-hydroxyphenyldimethyl-sulfonium methyl sulfate (hereunder, DSP). Specifically, 1 mol of dodecanedicarboxylic acid, 2 mol of DSP and 2 mol of dicyclohexylcarbodiimide (hereunder, DCCD) are dissolved in acetonitrile and the mixture is stirred at 25° C. for 5 hours for reaction. The dicyclohexylurea produced during the reaction process was removed with a glass filter. The reaction mixture (filtrate) was then solidified by dropwise addition into ether. The solid product was dried under reduced pressure to obtain the target crosslinking agent. The chemical structure and purity was confirmed by $^1$H-NMR.

Test Example 1

Cytotoxicity Test Using Water-Soluble Elastin and Crosslinking Agent

The MTT method, which is based on the principle that viable cells convert 3-(4,5-dimethyl-2-thiazolyl)-2,5-diphenyl-2H-tetrazolium bromide (hereunder, MTT) to a formazan product, was used as a toxicity test for the water-soluble elastin and crosslinking agent with respect to vascular smooth muscle cells. Since tetrazolium salts of MTT and the like can serve as substrates of dehydrogenase in the TCA cycle, which is an oxidative phosphorylation reaction in mitochondria, they allow measurement of the inhibition of sample substances on cell activity. A Cell Proliferation Kit I (Roche) was used for the measurement.

Figure 1:
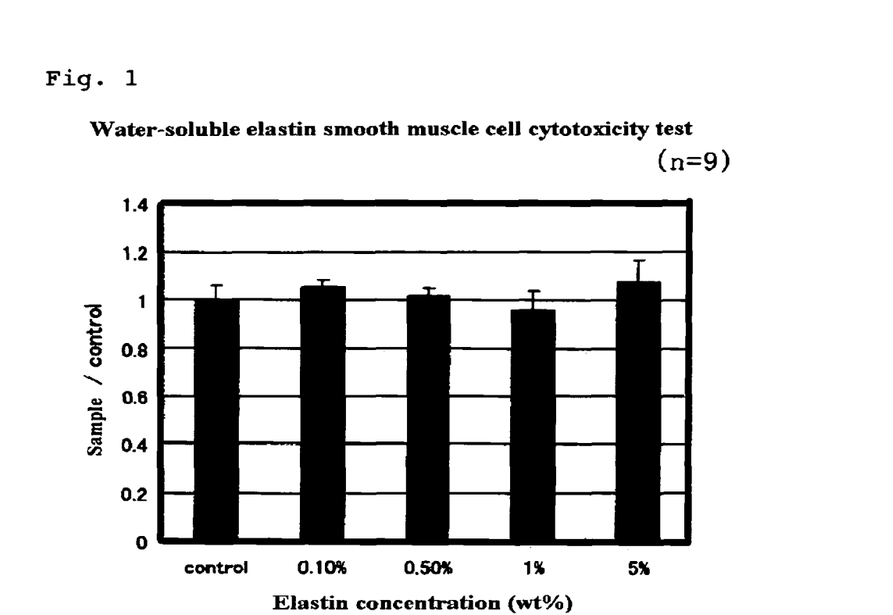
FIG. 1 is a bar graph showing the cytotoxicity test results for water-soluble elastin using MTT. The water-soluble elastin was judged to have no cytotoxicity.
Figure 2:
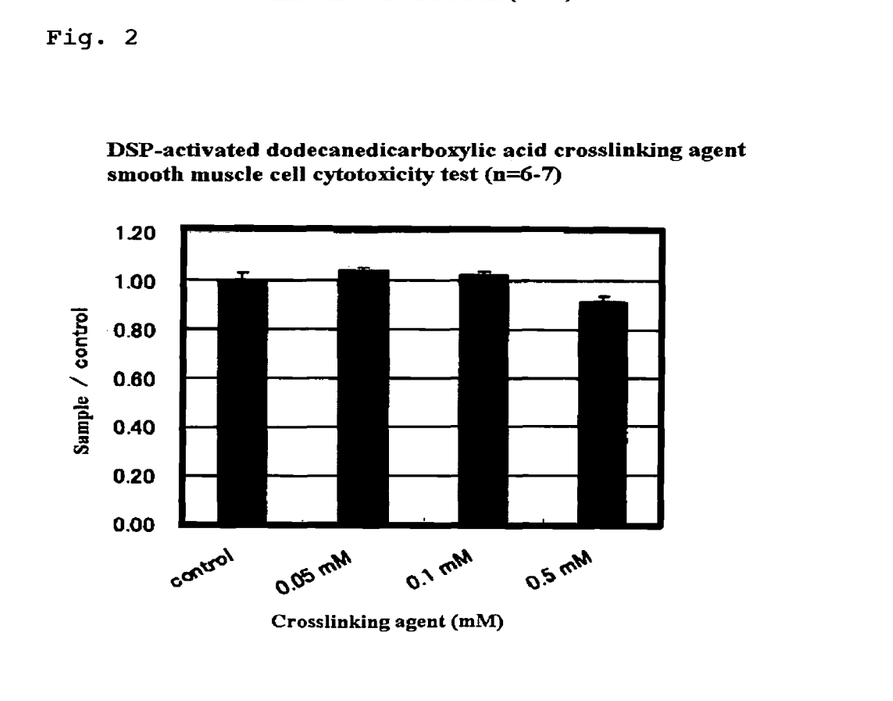
FIG. 2 is a bar graph showing the cytotoxicity test results for a crosslinking agent (DODE-DSP) using MTT. The crosslinking agent (DODE-DSP) was judged to have no cytotoxicity.
Figure 3:
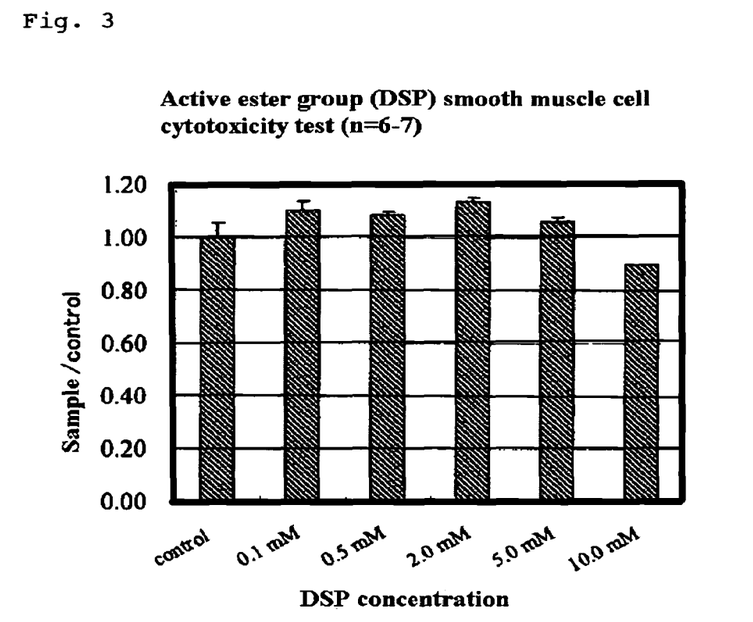
FIG. 3 is a bar graph showing the cytotoxicity test results for active ester group (DSP) using MTT. The active ester group (DSP) was judged to have no cytotoxicity.

As the specific measuring method, CSC culture medium (vascular smooth muscle cell culturing medium: product of Dainippon Pharmaceutical Co., Ltd.) containing 10 vol % fetal bovine serum was added to a 96 well cell culture plate at 100 µL/well and incubated, and then a smooth muscle cell suspension (cell density: $1.5 \times 10^5$ cells/mL) was seeded at 10 µL/well and culturing was carried out at 37° C. in a 5 vol % $CO_2$ incubator. Upon reaching subconfluence, the medium was aspirated, 100 µL of CSC medium containing 0.1 vol % fetal bovine serum was added, and culturing was continued for 24 hours in the incubator until cell growth ceased. After rinsing with PBS, the water-soluble elastin aqueous solution (concentration: 0.1-5 wt %) produced in Production Example 1, the DSP activated dodecanedicarboxylic acid crosslinking agent (50-500 µM) produced in Production Example 2 and the DSP (0.05-20 mM) used in Production Example 2 were added at 100 µL/well each, and culturing was continued for 24 hours in the incubator. The sample solution was then aspirated and rinsed with PBS, CSC medium containing 10 vol % fetal bovine serum was added to 100 µL/well, a specified amount of MTT solution was added prior to stationing overnight in the incubator, and a microplate reader was used for measurement of the absorbance at a measuring wavelength of 550 nm and a reference wavelength of 655 nm. A control was prepared without addition of sample and compared with the measured values. The results are shown in FIG. 1, FIG. 2 and FIG. 3. The water-soluble elastin, crosslinking agent and activeester group portion (DSP) were all essentially unchanged with respect to the control within the measured concentration range, or in other words, they had no effect on cell activation and exhibited no toxicity.

Test Example 2

Measurement of Coacervation Temperature of Water-Soluble Elastin

Figure 4:
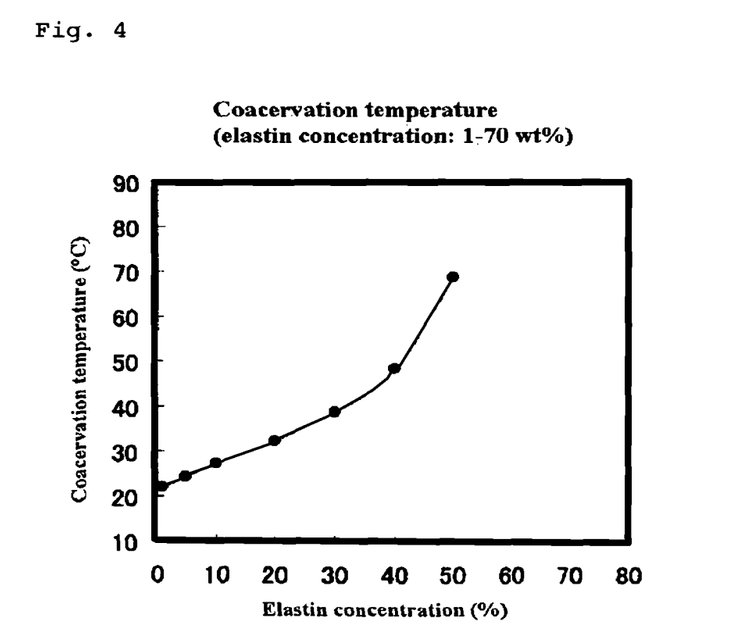
FIG. 4 is a graph showing the results of measuring the coacervation temperature (elastin concentration: 0.1-70 wt %). No coacervation temperature is exhibited at 60% and greater because of the non-agglutinating liquid.

Water-soluble elastin exhibited a heat-sensitive phenomenon of hydrophobic interaction and aggregation within the molecules or between molecules with increasing solution temperature. This is referred to as "coacervation", and is known as an important phenomenon in water-soluble elastin. The coacervation temperature can be determined by measuring the solution turbidity. Specifically, a spectrophotometer with a temperature-variable device was used for irradiation of the sample solution with a specific wavelength (640 nm), and the proportion of transmitted light intensity with respect to incident light intensity was calculated as the transmittance. The transmittance was measured while varying the temperature from 10-80° C., and the temperature at which the transmittance reduction was 50% of the total was defined as the coacervation temperature. The coacervation temperature was measured while varying the elastin concentration from 0.1-70 wt %. The results are shown in FIG. 4. It was confirmed that the coacervation temperature increased with increasing water-soluble elastin concentration, with no aggregation at 60 wt % and higher. These results demonstrated that with a water-soluble elastin concentration of 60 wt % or greater, the water-soluble elastin crosslinked at a temperature of 100° C. or above to obtain a transparent molded article.

Example 1

Preparation of Elastin-Coated Dish for Static Cell Culturing

The following procedure was followed under aseptic conditions on a clean bench. The surface of a 35ϕ dish for suspension culture (product of Sumitomo Bakelite Co., Ltd., polystyrene material) was subjected to discharge (9 kV) treatment for 45 seconds with the corona flame blow-out hole of a corona discharge apparatus (CoronaFit: product of Shinko Electric & Instrumentation Co., Ltd.) kept at a distance of 10 mm from the culturing dish surface, and then 1 mL of a 100 µg/mL water-soluble elastin solution was allowed to stand therein for 8 hours. The elastin solution was then discarded and the dish was dried at room temperature for about 1 hour. This treatment results in reaction and anchoring of elastin onto the dish surface that has been activated by the corona discharge, so that it becomes coated with elastin. As a control experiment there was also prepared a collagen-coated dish. The coated state was evaluated by measuring the water droplet contact angle on the surface. Specifically, a 35ϕ suspension culture dish was placed on slide glass situated on the placement stage of a contact angle measuring instrument (by ERMA Corp.), 20 µL of deionized water was added with a microburet, and the contact angle was measured after allowing it to stand for several seconds. The average value of 5 contact angle measurements was recorded as the measured value.

Figure 5:
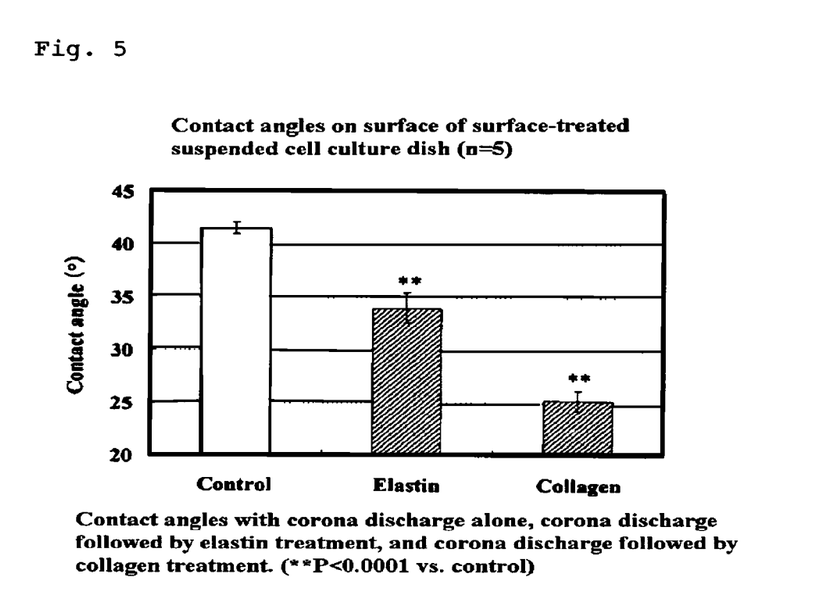
FIG. 5 is a bar graph showing the results of measuring the water droplet contact angle on the surface of a sample subjected only to corona discharge (Control), a sample subjected to corona discharge and then elastin treatment (Elastin) and a sample subjected to corona discharge and then collagen treatment (Collagen), in a polystyrene culturing dish. (**P<0.0001 vs. control)

Elastin and collagen were anchored onto the surface by activating the hydrophobic surface by corona discharge and reacting it with protein in water. Restoration to the original hydrophobicity in air was observed at approximately 8 hours after discharge (contact angle: approximately 80°). When water alone was added immediately after discharge (control), a portion of the water molecules slowly reacted during restoration to the original hydrophobicity producing a hydrophilic state, and surface change was stabilized at about 8 hours, with a contact angle of about 42°. With immersion in an elastin aqueous solution or collagen aqueous solution immediately after discharge, the contact angles were 25° and 34° respectively after 8 hours, and thus a stabilized surface had been formed in a more hydrophilic state than the control (FIG. 5). These results confirmed that elastin and collagen had been coated onto the corona discharge treated dish surface.

Example 2

Production of Dynamic Culture Device Using Elastin-Coated Silicon Sheet

Figure 6:
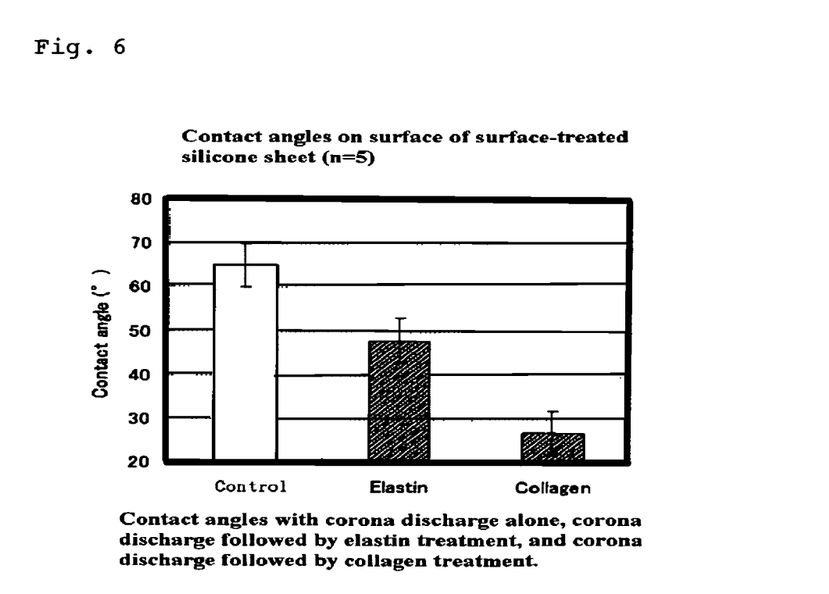
FIG. 6 is a bar graph showing the results of measuring the water droplet contact angle on the surface of a sample subjected only to corona discharge (Control), a sample subjected to corona discharge and then elastin treatment (Elastin) and a sample subjected to corona discharge and then collagen treatment (Collagen), in a culturing dish with a silicon sheet bottom.

A 10 mm-thick silicon rubber sheet was prepared and used to form a box-like enclosure for a culture dish with dimensions of 3 cm length×3 cm width×1 cm height. A 50 µm-thick silicon rubber sheet was attached to the bottom using Bathcoke (HJ-132 by Cemedine Co., Ltd.), and this was allowed to stand for a day for complete attachment. After thorough washing with deionized water, autoclave treatment was carried out at 121° C. for 30 minutes for sterilization. The same corona discharge apparatus of Example 1 was used for 45 seconds of surface treatment, and after adding 1 mL of a 100 μg/mL water-soluble elastin solution and collagen solution, the dish was allowed to stand for 8 hours. As a control experiment there was also prepared a collagen-coated dish. The coating was evaluated based on the measured contact angle (FIG. 6). Since a significant reduction in contact angle is also seen with a silicon sheet as for the suspension culture dish, it was confirmed that elastin and collagen had been coated.

Example 3

Production of Dynamic Culture Device Using Elastin Gel Sheet

After adding 240 μL of a 340 mM aqueous solution of the crosslinking agent produced in Production Example 2 to 600 mg of water-soluble elastin, deionized water was further added to prepare a solution with a final elastin concentration of 65 wt %. A template was formed with a glass plate treated for water-repellency on both sides, and the elastin solution was cast into a sheet form and subjected to heat crosslinking at 100° C. for 30 minutes to obtain an optically transparent elastin gel sheet with a film thickness of about 100 μm. The conditions were such as to avoid coacervation, and the transmittance of the elastin gel sheet for visible light was about 60-90%, allowing observation under an optical microscope. An enclosure for a culture dish with dimensions of 3 cm length×3 cm width×1 cm height was produced using a 10 mm-thick silicon rubber sheet, similar to the one prepared in Example 2, and the elastin gel sheet was attached thereto with an adhesive. After thorough washing with deionized water, autoclave treatment was carried out at 121° C. for 30 minutes for sterilization.

Example 4

Vascular Cell Culturing Adhesion/Stretch Test

Commercially available normal human vascular smooth muscle cells, normal human fibroblasts and normal human vascular endothelial cells were seeded at $1.0 \times 10^4$ (cells/mL), together with special serum-free medium, onto an elastin-coated dish and a collagen-coated dish, as prepared in Example 1. Culturing was carried out with a 5% $CO_2$ culturing apparatus (OLYMPUS MI-IBC) while inputting an image from an optical microscope (OLYMPUS IMT-2) to personal computer XCAP software, with a set number of photographs and photographing interval. The time at seeding was defined as 0, and the photographed images were analyzed with Adobe Photoshop. The cell adhesion and stretch of the attached cells were evaluated based on analysis of the photographed images. This the total number of adhering cells at each time point and the number of distended cells were measured from the chronologically photographed cell images, and values for the adhesion (%)=(number of adhering cells/total number of cells)×100 and the stretch (%)=(number of distended cells/total number of cells)×100 were calculated.

The adhesion was judged in the following manner. The cells immediately after seeding are spherical, but generate desmosomes at the first change. When the cells extend pseudopods to the matrix and the surface receptor integrin binds to the matrix, integrin aggregates to form desmosomes at the high density region points. The shapes of the cells are essentially spherical. This was defined as the attached state.

As the second change, when all of the integrin at the sections between the cells and matrix has become attached, desmosomes form over the entire cell membrane such that the cells undergo a change in shape to a non-spherical shape. This is the distended state. The adhesion and stretch is evaluated based on these two changes.

Figure 7:
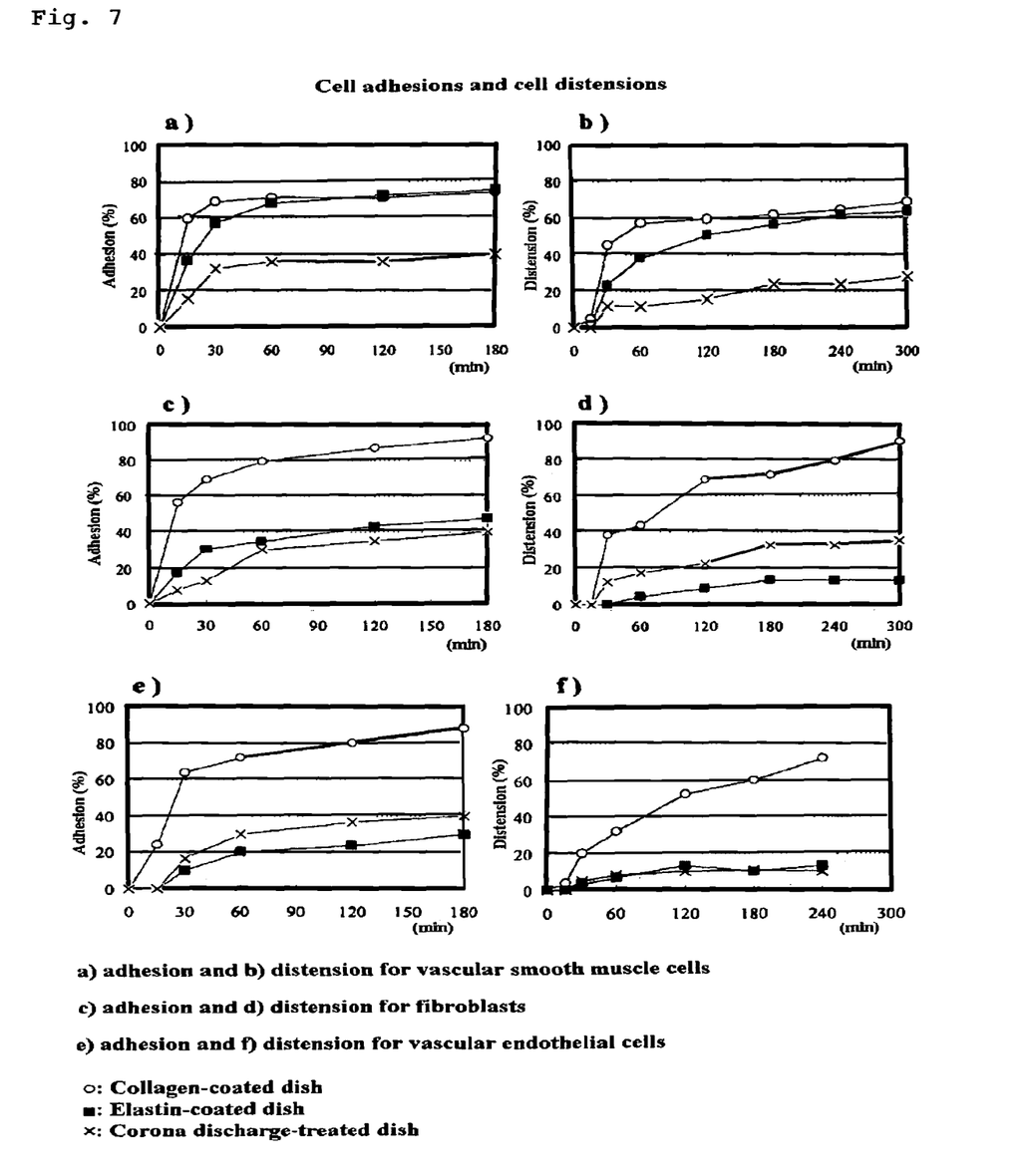
FIG. 7 is a set of graphs showing the results of measuring the adhesion and distensibility of vascular cells on a surface-treated polystyrene culturing dish. It shows the a) adhesion and b) distensibility of vascular smooth muscle cells, the c) adhesion and d) distensibility of fibroblasts and the e) adhesion and f) distensibility of vascular arterial endothelial cells. ○ represents samples subjected to corona discharge and then collagen treatment, ■ represents samples subjected to corona discharge and then elastin treatment, and x represents samples subjected only to corona discharge.

The results of determining the adhesion and stretch of each cell type for the elastin- (or collagen)-coated dish are shown in FIG. 7. The vascular smooth muscle cells were observed to exhibit high adhesion (≥63% after 1 hour) and stretch (≥62% after 4 hours) for the elastin surface and collagen surface. In particular, it was found that adhesion and stretch were essentially complete with about 1 hour and within 4 hours, respectively. With fibroblasts, high adhesion (≥80% after 1 hour) and stretch (≥80% after 4 hours) were confirmed with respect to the collagen surface, but with respect to the elastin surface, low adhesion (34.8% after 1 hour) and stretch (13.0% after 4 hours) were exhibited similar to the dish that had only been corona discharge treated. With vascular endothelial cells, the same tendency was exhibited as with fibroblasts. Specifically, high adhesion (≥72% after 1 hour) and stretch (≥72% after 4 hours) were exhibited with respect to the collagen surface, but with respect to the elastin surface, low adhesion (20.0% after 1 hour) and stretch (13.3% after 4 hours) were exhibited.

These results are shown in Table 1, wherein adhesion of 50% or greater after 1 hour and stretch of 50% or greater after 4 hours is represented by ○, and adhesion of up to 50% after 1 hour and stretch of up to 50% after 4 hours is represented by x. The cell instrument having elastin on the surface, as the invention product, clearly has a high degree of recognition as an extracellular matrix for vascular smooth muscle cells.

TABLE 1

|  | Vascular smooth muscle cells | Fibroblasts | Vascular endothelial cells |
| --- | --- | --- | --- |
| Discharge only | X | X | X |
| Elastin | ○ | X | X |
| Collagen | ○ | ○ | ○ |

Example 5

Figure 8:
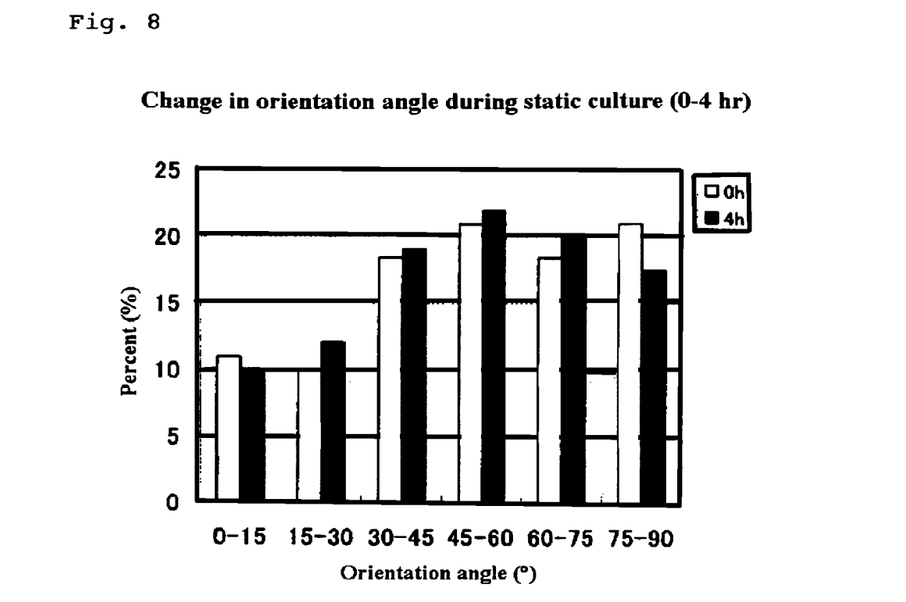
FIG. 8 is a bar graph showing the results of measuring the change in orientation angle (0-4 hour) during static culturing.
Figure 9:
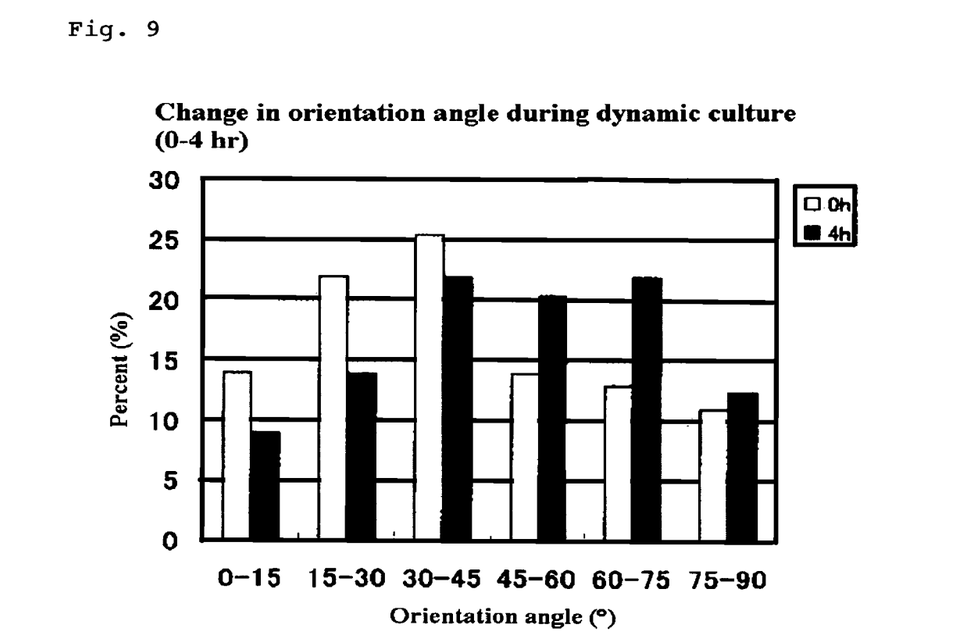
FIG. 9 is a bar graph showing the results of measuring the change in orientation angle (0-4 hour) during dynamic culturing. The stretch conditions were a cycle of 0.5 Hz and a distensibility of 10%.

Dynamic Culturing Test with Dynamic Culture Device Using Elastin-Coated Silicon Sheet In a dynamic culture device employing the elastin-coated silicon sheet prepared in Example 2, with CSC medium (vascular smooth muscle cell medium: product of Dainippon Pharmaceutical Co., Ltd.), there was seeded 1 mL of a vascular smooth muscle cell suspension prepared to a cell density of $1.0 \times 10^5$ (cells/mL). At 20 hours after seeding the cells, static culturing was carried out at 37° C. in a 5% $CO_2$ culturing apparatus (OLYMPUS MI-IBC). Upon removing the dynamic culture device and confirming adhesion of the cells using a phase contrast microscope, the medium was exchanged with 3 mL of CSC medium and static culturing was continued for 4 hours at 37° C., 5% $CO_2$ for incubation. Next, the static-cultured dynamic culture device was set in a dynamic cell culturing apparatus fixed to a microscope stage, and dynamic cell culturing (uniaxial stretch culturing) was carried out for 4 hours with stretching conditions of 1 cycle every 2 seconds (0.5 Hz) at 10% stretch, with repeated photographing of the same location. Analysis of the photographed images allowed measurement of the orientation angle of the vascular smooth muscle cells in the direction of tension application at each time point during dynamic culturing. FIG. 8 shows the change in orientation angle during static culturing (0-4 hour), and FIG. 9 shows the change in orientation angle during dynamic culturing (0-4 hour). Almost no change in angle occurred in the static culturing, but based on the orientation angle distribution during the dynamic culturing, the proportion of cells oriented at a vertical angle with respect to the direction of tension application was found to increase with time. Also, no change was seen under stretching conditions of 0.5 Hz, 0.2%, similar to the static culturing.

Example 6

Vascular Smooth Muscle Differentiation Inducing Test

Figure 10:
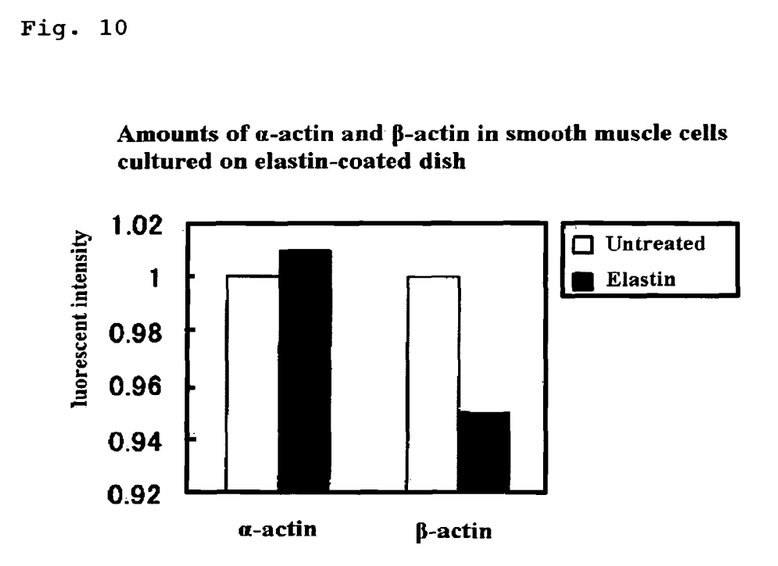
FIG. 10 is a bar graph showing the results of assaying $\alpha$-actin and $\beta$-actin in smooth muscle cells cultured on an elastin-coated dish.

As an experiment to examine cytoskeleton structure changes in vascular smooth muscle cells, immunostaining of the cytoskeletal proteins α-actin and β-actin was carried out, and the protein was assayed by pixel analysis of the obtained images. Ordinarily, α-actin is characterized by differentiation while β-actin is mostly dedifferentiated. The amounts of both actins expressed in vascular smooth muscle cells cultured on an elastin-coated dish prepared by the method of Example 1 were divided by the amounts of both actins expressed in vascular smooth muscle cells cultured in a common adhesive cell dish (product of Sumitomo Bakelite Co., Ltd., hydrophilic treated polystyrene) as a control, and the ratios were as shown in FIG. 10.

Specifically, this was carried out as follows. Smooth muscle cells were seeded in an elastin-coated culture dish prepared by the method of Example 1 and cultured to subconfluence, and then the medium was removed by aspiration and rinsed with PBS, after which it was immersed in glutaraldehyde-containing fixing solution for 30 minutes and the fixing solution was removed, prior to drying. To the cells there was added 200 µL of primary antibody (mouse anti-human α-actin antibody) and (mouse anti-human β-actin antibody), for immersion overnight. Next, using 200 µL each of FITC-labeled antimouse antibody as green secondary antibody for α-actin, and rhodamine-labeled anti-mouse antibody as red secondary antibody for β-actin, binding was carried out for 60 minutes in a dark location, followed by rinsing and drying, and then observation under a fluorescent microscope.

The smooth muscle cells cultured on elastin, even without dynamic culturing, had increased α-actin and reduced β-actin compared with the actin in the untreated culture dish, thus indicating that differentiation had been induced.

Example 7

Dynamic Culturing Test with Dynamic Culture Device Using Elastin Gel Sheet

Vascular smooth muscle cells were cultured in the same manner as Example 5, using a dynamic culture device employing the elastin gel sheet prepared in Example 3. It was possible to perform three-dimensional microscope observation of the cells growing on the elastin gel sheet.

The invention claimed is:
1. A method of proliferating vascular smooth muscle cells, comprising the steps of:
    (i) culturing a mixture of vascular smooth muscle cells and other vascular cells on a substrate comprising elastin under a static condition in which the elastin and substrate neither expands nor contracts,
    (ii) after the mixture of cells has become bound to the elastin, culturing the mixture of cells under a dynamic condition in which the elastin and substrate expands and contracts, and
    (iii) selecting for proliferated vascular smooth muscle cells,
    wherein the vascular smooth muscle cells are selectively proliferated more than the other vascular cells in the mixture.

* * * * *